(12) United States Patent
Sakamoto

(10) Patent No.: US 10,555,723 B2
(45) Date of Patent: Feb. 11, 2020

(54) IMAGING APPARATUS FOR DIAGNOSIS, CONTROL METHOD THEREFOR, PROGRAM, AND COMPUTER READABLE STORAGE MEDIUM

(71) Applicant: TERUMO KABUSHIKI KAISHA, Shibuya-ku, Tokyo (JP)

(72) Inventor: Masayuki Sakamoto, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 337 days.

(21) Appl. No.: 15/706,009

(22) Filed: Sep. 15, 2017

(65) Prior Publication Data

US 2018/0014815 A1    Jan. 18, 2018

Related U.S. Application Data

(63) Continuation of application No. PCT/JP2016/057989, filed on Mar. 14, 2016.

(30) Foreign Application Priority Data

Mar. 24, 2015   (JP) ................................. 2015-061608

(51) Int. Cl.
*A61B 8/08*     (2006.01)
*A61B 8/12*     (2006.01)
(Continued)

(52) U.S. Cl.
CPC .......... *A61B 8/5261* (2013.01); *A61B 5/0084* (2013.01); *A61B 5/066* (2013.01);
(Continued)

(58) Field of Classification Search
CPC .. A61B 1/00; A61B 8/12; A61B 8/461; A61B 8/4405; A61B 8/13; A61B 8/5261;
(Continued)

(56) References Cited

U.S. PATENT DOCUMENTS 6,575,969 B1 *  6/2003  Rittman, III ....... A61B 18/1482
                                                    606/41
7,289,842 B2    10/2007  Maschke
(Continued)

FOREIGN PATENT DOCUMENTS

JP    2014-180575 A    9/2014
WO    2008/057573 A2   5/2008
(Continued)

OTHER PUBLICATIONS

The extended European Search Report dated Nov. 9, 2018, by the European Patent Office in corresponding European Patent Application No. 16768527.0-1124. (8 pages).
(Continued)

*Primary Examiner* — Bo Joseph Peng
(74) *Attorney, Agent, or Firm* — Buchanan Ingersoll & Rooney PC

(57) ABSTRACT

A control method, computer readable medium, and imaging apparatus for diagnosis being configured to create a tomographic image are disclosed. The method includes obtaining ultrasound line data oriented in a radial direction from a rotation center based on a signal obtained by executing the scanning; obtaining optical interference line data oriented in a radial direction from the rotation center based on a signal obtained by executing the scanning; identifying a line or a group of lines having a same feature out of each line data of the ultrasound tomographic image and the optical tomographic image; determining segmentation positions for a bundle of lines corresponding to at least a single frame included in each tomographic image from each line data of the ultrasound tomographic image and the optical tomographic image with respect to the identified line or group of lines; and creating a tomographic image from the determined bundle of lines.

20 Claims, 8 Drawing Sheets

(51) Int. Cl.
    *A61B 5/00*    (2006.01)
    *A61B 5/06*    (2006.01)
    *A61B 8/13*    (2006.01)
    *A61B 8/00*    (2006.01)
(52) U.S. Cl.
    CPC .......... *A61B 5/6851* (2013.01); *A61B 5/6852* (2013.01); *A61B 5/6862* (2013.01); *A61B 5/742* (2013.01); *A61B 8/12* (2013.01); *A61B 8/13* (2013.01); *A61B 8/4405* (2013.01); *A61B 8/461* (2013.01)
(58) Field of Classification Search
    CPC ..... A61B 5/6852; A61B 5/6851; A61B 5/066; A61B 5/0084; A61B 5/742
    See application file for complete search history.

(56) References Cited

U.S. PATENT DOCUMENTS

| 8,126,534 | B2 | 2/2012 | Maschke |
| 9,375,164 | B2 * | 6/2016 | Tolkowsky ............. A61B 5/06 |
| 2010/0157041 | A1 * | 6/2010 | Klaiman ............. A61B 5/0044 348/77 |
| 2010/0256504 | A1 * | 10/2010 | Moreau-Gaudry ......................... A61B 5/0066 600/476 |
| 2014/0276020 | A1 | 9/2014 | Hutchins et al. |
| 2015/0051485 | A1 | 2/2015 | Itoh et al. |
| 2015/0196285 | A1 | 7/2015 | Mori |

FOREIGN PATENT DOCUMENTS

| WO |  2009/009802 A1 | 1/2009 |
| WO | WO 2013/145635 A1 | 10/2013 |
| WO | WO 2014/049644 A1 | 4/2014 |

OTHER PUBLICATIONS

International Search Report (PCT/ISA/210) dated May 17, 2016, by the Japanese Patent Office as the International Searching Authority for International Application No. PCT/JP2016/057989.

Written Opinion (PCT/ISA/237) dated May 17, 2016, by the Japanese Patent Office as the International Searching Authority for International Application No. PCT/JP2016/057989.

* cited by examiner

IMAGING APPARATUS FOR DIAGNOSIS, CONTROL METHOD THEREFOR, PROGRAM, AND COMPUTER READABLE STORAGE MEDIUM

CROSS-REFERENCES TO RELATED APPLICATIONS

This application is a continuation of International Application No. PCT/JP2016/057989 filed on Mar. 14, 2016, which claims priority to Japanese Application No. 2015-061608 filed on Mar. 24, 2015, the entire contents of which are incorporated herein by reference.

TECHNICAL FIELD

The present disclosure relates to an imaging apparatus for diagnosis, a control method therefore, a program, and a computer readable storage medium.

BACKGROUND ART

In the related art, an imaging apparatus for diagnosis has been widely used for diagnosis of arteriosclerosis, for pre-operative diagnosis at the time of intravascular treatment using a high performance catheter such as a balloon catheter or stent, or for checking a result after the surgical operation.

The imaging apparatus for diagnosis can include an intravascular ultrasound (IVUS) diagnostic apparatus and an optical coherence tomography (OCT) diagnostic apparatus, each having different characteristics.

Recently, an imaging apparatus for diagnosis having a combination of the IVUS function and the OCT function has been proposed. Such an imaging apparatus for diagnosis has an imaging core that rotatably accommodates an ultrasound transceiver capable of transmitting or receiving an ultrasound wave and an optical transceiver capable of transmitting or receiving light at a distal end position of the catheter. In the case of such an imaging apparatus for diagnosis having both functions, both a cross-sectional image taking advantage of the IVUS characteristics, that is, a capability of measurement up to a high depth region, and a cross-sectional image taking advantage of the OCT characteristics, that is, a capability of measurement with a high resolution, can be created through a single scanning operation.

However, due to influences of a distance between the ultrasound transceiver and the optical transceiver, installation precisions of the ultrasound transceiver and the optical transceiver, a deviation in the emitting direction, it can be difficult to arrange the IVUS tomographic image obtained by the IVUS function and the OCT tomographic image obtained by the OCT function in the same orientation. In this regard, there is also known a technique of rotating these images until a distance between a landmark of the blood vessel wall in the IVUS tomographic image and a landmark of the blood vessel wall in the OCT tomographic image is minimized (for example, JP-A-2014-180575).

However, in the technique of JP-A-2014-180575, although the orientations of the tomographic images are aligned, a part of the image visualizes a blood vessel wall at a position shifted by one cycle from each other. That is, in one of the images, the shifted part corresponds to the initial part out of the scanning of one revolution constituting one frame of a tomographic image. Meanwhile, in the other image, the shifted part corresponds to the last part out of the scanning of one revolution.

SUMMARY OF THE DISCLOSURE

The present disclosure is made in view of the aforementioned problems and provides a technology for creating an ultrasound tomographic image and an optical tomographic image aligned in the same orientation at the closest axial position.

In order to address the aforementioned problems, for example, a control method of an imaging apparatus for diagnosis according to the disclosure has the following configuration. In accordance with an exemplary embodiment, a control method of an imaging apparatus for diagnosis is disclosed, the imaging apparatus for diagnosis being configured to create an ultrasound tomographic image and an optical tomographic image inside an examination target object to which an imaging core moves by performing scanning using a probe that houses the imaging core provided with an ultrasound transceiver and an optical transceiver by moving the imaging core along an axial direction of the probe while rotating the imaging core, the control method including: a process of obtaining ultrasound line data oriented in a radial direction from a rotation center on the basis of a signal obtained by executing the scanning; a process of obtaining optical interference line data oriented in a radial direction from the rotation center on the basis of a signal obtained by executing the scanning; a process of identifying a line or a group of lines having the same feature out of each line data of the ultrasound tomographic image and the optical tomographic image; a process of determining segmentation positions for a bundle of lines corresponding to at least a single frame included in each tomographic image from each line data of the ultrasound tomographic image and the optical tomographic image with respect to the identified line or group of lines; and a process of creating a tomographic image from the determined bundle of lines.

A non-transitory computer readable storage medium containing a computer program having computer readable code embodied to carry out a method of controlling an imaging apparatus for diagnosis, the imaging apparatus for diagnosis being configured to create an ultrasound tomographic image and an optical tomographic image inside an examination target object to which an imaging core moves by performing scanning using a probe that houses the imaging core provided with an ultrasound transceiver and an optical transceiver by moving the imaging core along an axial direction of the probe while rotating the imaging core, the method of controlling the imaging apparatus for diagnosis comprising: obtaining ultrasound line data oriented in a radial direction from a rotation center on a basis of a signal obtained by executing the scanning; obtaining optical interference line data oriented in a radial direction from the rotation center on a basis of a signal obtained by executing the scanning; identifying a line or a group of lines having a same feature out of each line data of the ultrasound tomographic image and the optical tomographic image; determining segmentation positions for a bundle of lines corresponding to at least a single frame included in each tomographic image from each line data of the ultrasound tomographic image and the optical tomographic image with respect to the identified line or group of lines; and creating a tomographic image from the determined bundle of lines.

An imaging apparatus for diagnosis configured to create an ultrasound tomographic image and an optical tomographic image inside an examination target object to which an imaging core moves by performing scanning using a probe that houses the imaging core provided with an ultrasound transceiver and an optical transceiver by moving the imaging core along an axial direction of the probe while rotating the imaging core, the imaging apparatus comprising: a processor configured to: obtain ultrasound line data oriented in a radial direction from a rotation center on a basis of a signal obtained by executing the scanning; obtain optical interference line data oriented in the radial direction from the rotation center on a basis of a signal obtained by executing the scanning; identify a line or a group of lines having a same feature out of each line data of the ultrasound tomographic image and the optical tomographic image; determine segmentation positions for a bundle of lines corresponding to at least a single frame included in each tomographic image from each line data of the ultrasound tomographic image and the optical tomographic image with respect to the identified line or group of lines; and create a tomographic image from the determined bundle of lines.

According to the disclosure, an ultrasound tomographic image and an optical interference tomographic image aligned in the same orientation can be created and at the same position with relatively higher efficiency and accuracy compared to the known art.

Other features and advantages of the present disclosure will become apparent by reading the following description with reference to the accompanying drawings. Note that like reference numerals denote like elements throughout the drawings.

BRIEF DESCRIPTION OF THE DRAWINGS

The accompanying drawings, which are incorporated in and constitute a part of this specification, illustrate embodiments of the disclosure and, together with the description, serve to explain the principle of the disclosure.

DETAILED DESCRIPTION

Each embodiment of the disclosure will now be described in details with reference to the accompanying drawings. Note that, in the following embodiments, although various technically preferable limitations are added for specific preferable examples of the disclosure, the scope of the disclosure is not limited to such aspects unless there is a statement for particularly limiting the disclosure.

Embodiments of the disclosure will now be described in details with reference to the accompanying drawings. Note that, herein, it is assumed that an imaging apparatus for diagnosis has both an intravascular ultrasound (IVUS) function and an optical coherence tomographic (OCT) function.

Figure 1:
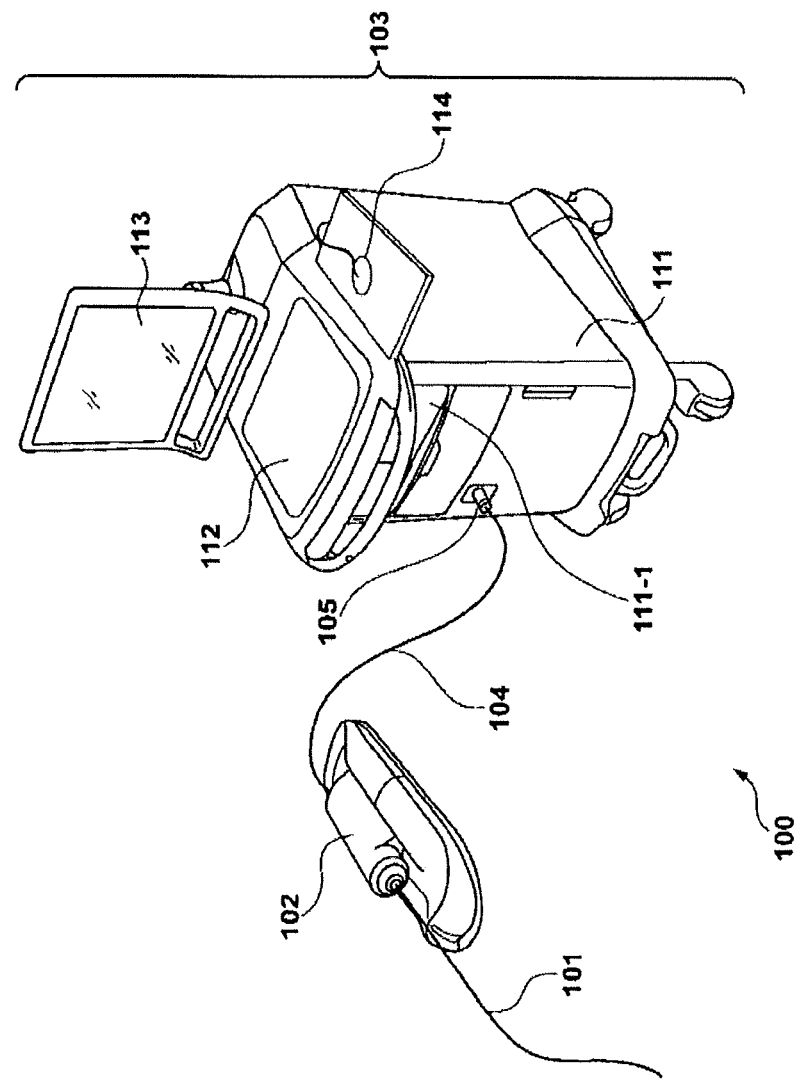
FIG. 1 is a diagram illustrating an exterior configuration of an imaging apparatus for diagnosis according to an exemplary embodiment.

FIG. 1 is a diagram illustrating an exterior configuration of an imaging apparatus for diagnosis 100 according to an exemplary embodiment of the disclosure.

As illustrated in FIG. 1, the imaging apparatus for diagnosis 100 can include a probe 101, a pull-back unit 102, and an operation control apparatus 103. The pull-back unit 102 and the operation control apparatus 103 are connected to each other with a connector 105 through a signal line or an optical fiber cable 104.

The probe 101 is directly inserted into a blood vessel and houses an imaging core which is movable in its longitudinal direction and rotatable. At a distal end of the imaging core, an ultrasound transceiver that transmits an ultrasound wave based on a pulse signal and receives a reflection wave from the blood vessel, and an optical transceiver that continuously transmits the received light (measurement light) to the blood vessel and continuously receives the reflection light from the blood vessel are installed. The imaging apparatus for diagnosis 100 measures an intravascular state by using the imaging core.

The pull-back unit 102 is detachably installed with the probe 101 and defines an axial intravascular operation and a rotational intravascular operation of the imaging core inside a catheter inserted into the probe 101 by driving an internal motor. In addition, the pull-back unit 102 serves as a signal relay unit between the ultrasound transceiver and the optical transceiver of the imaging core and the operation control apparatus 103. That is, the pull-back unit 102 has a function of transmitting an ultrasound drive signal from the operation control apparatus 103 to the ultrasound transceiver and transmitting an electric signal representing a reflection wave from a biological tissue detected by the ultrasound transceiver to the operation control apparatus 103. In addition, the pull-back unit 102 has a function of transmitting the measurement light from the operation control apparatus 103 to the optical transceiver and transmitting the reflection light from the biological tissue detected by the optical transceiver to the operation control apparatus 103.

The operation control apparatus 103 has a function for entering various setting values to perform measurement or a function for processing the ultrasound data or the optical interference data obtained through measurement and displaying various vascular images.

The operation control apparatus 103 has a main body control unit 111. The main body control unit 111 creates line data oriented in a radial direction from a rotation center position based on a reflection wave signal of the ultrasound wave obtained through the measurement. In addition, the main body control unit 111 creates an ultrasound tomographic image by interpolating each line data. Furthermore, the main body control unit 111 creates interference light data by causing the reflection light from the imaging core and the reflection light obtained by separating light from a light source to interfere with each other and creates line data by performing a fast Fourier transform (FFT) for the interference light data. In addition, the main body control unit 111 creates the optical tomographic image through an interpolation process.

In accordance with an exemplary embodiment, an element 111-1 is a printer and DVD recorder that outputs the data to the outside by printing a processing result of the main body control unit 111 or recording it on a digital versatile disc (DVD). In addition, the printer and DVD recorder 111-1 has an interface (not shown) such as a universal serial bus (USB) to output the data to an external storage medium therefrom. An element 112 is an operation panel 112, which can be used by a user to enter various setting values and instructions. An element 113 is an LCD monitor 113 as a display unit that displays various cross-sectional images created by the main body control unit 111. An element 114 is a mouse 114 serving as a pointing device (coordinates input device).

Figure 2:
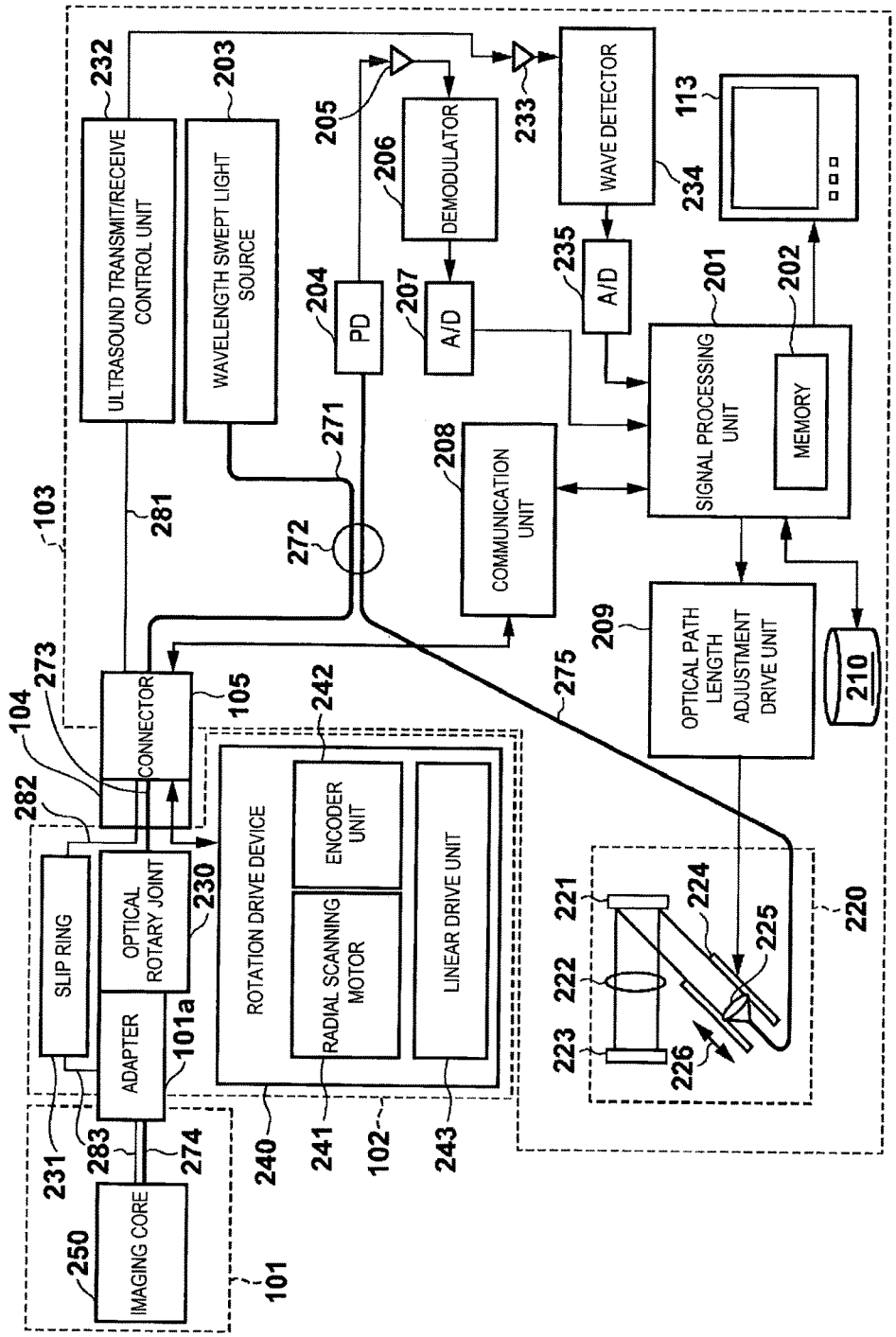
FIG. 2 is a block diagram illustrating an imaging apparatus for diagnosis according to an exemplary embodiment.

Next, a functional configuration of the imaging apparatus for diagnosis 100 will be described. FIG. 2 is a block diagram illustrating the imaging apparatus for diagnosis 100. A functional configuration of a wavelength swept optical coherence tomographic (OCT) will be described with reference to FIG. 2.

In FIG. 2, an element 201 is a signal processing unit that controls the entire imaging apparatus for diagnosis and has several circuits including a microprocessor. An element 210 is a non-volatile storage device such as a hard disk that stores various programs or data files executed by the signal processing unit 201. An element 202 is a memory (RAM) provided in the signal processing unit 201. An element 203 is a wavelength swept light source which is a light source configured to repeatedly generate light having a wavelength that changes within a predetermined range along a time axis.

The light output from the wavelength swept light source 203 is incident to one end of a first single mode fiber 271 and is transmitted to a distal end side. The first single mode fiber 271 is optically coupled with a fourth single mode fiber 275 of the optical fiber coupler 272 provided in the middle.

The light incident to the first single mode fiber 271 and emitted from the optical fiber coupler 272 to the distal end side is guided to a second single mode fiber 273 through the connector 105. The other end of the second single mode fiber 273 is connected to an optical rotary joint 230 of the pull-back unit 102.

In accordance with an exemplary embodiment, the probe 101 has an adapter 101a for connection to the pull-back unit 102. In addition, by connecting the probe 101 to the pull-back unit 102 using this adapter 101a, the probe 101 is stably held in the pull-back unit 102. In addition, an end portion of a third single mode fiber 274 rotatably housed in the probe 101 is connected to the optical rotary joint 230. As a result, the second and third single mode fibers 273 and 274 are optically coupled to each other. The imaging core 250 having the optical transceiver (which will be described below in more details with reference to FIG. 5) provided with mirrors and lenses to emit light substantially in parallel with the rotation axis is provided in the other side of the third single mode fiber 274 (in the tip side of the probe 101).

As a result, the light emitted from the wavelength swept light source 203 is guided to the imaging core 250 provided in the end portion of the third single mode fiber 274 through the first single mode fiber 271, the second single mode fiber 273, and the third single mode fiber 274. The optical transceiver of the imaging core 250 emits this light in parallel to the axis of the fiber and receives its reflection light. In addition, the received reflection light is guided reversely and returns to the operation control apparatus 103.

Meanwhile, an optical path length adjustment mechanism 220 for minutely adjusting an optical path length of the reference light is provided in the opposite end portion of the fourth single mode fiber 275 coupled to the optical fiber coupler 272. The optical path length changing mechanism 220 serves as an optical path length changing means capable of changing an optical path length corresponding to a deviation of the length in order to absorb a deviation of the length of the individual probe 101 in the event of replacement of the probe 101. For this reason, a collimator lens 225 placed in the end portion of the fourth single mode fiber 275 is provided on a movable one-axis stage 224 as indicated by the arrow 226 arranged in its axial direction.

Specifically, the one-axis stage 224 serves as an optical path length changing means having a variable range of the optical path length as long as a deviation of the optical path length of the probe 101 can be absorbed in the event of replacement of the probe 101. In addition, the one-axis stage 224 also serves as an offset adjustment means. For example, the reflection light from a surface position of a biological tissue can be interfered with the reference light by minutely changing the optical path length using the one-axis stage even when a tip of the probe 101 does not abut on a surface of a biological tissue.

The light reflected on the mirror 223 through a grating 221 and a lens 222 by minutely adjusting the optical path length using the one-axis stage 224 is guided to the fourth single mode fiber 275 again and is mixed with the light obtained from the second single mode fiber 273 in the optical fiber coupler 272, so that the mixed light is received by the photodiode 204 as interference light.

In accordance with an exemplary embodiment, the interference light received by the photodiode 204 in this manner is photoelectrically converted by an amplifier 205 and is then input to a demodulator 206. The demodulator 206 performs a demodulation process for extracting only signal parts from the interference light, and its output is input to an A/D converter 207 as an interference light signal.

The A/D converter 207 creates a single line of digital data (interference light data) by sampling the interference light signal at a frequency of, for example, 90 MHz as many as 2,048 points. Note that the sampling frequency can be set, for example, to 90 MHz under the assumption that approximately 90% of a period (for example, 25 μsec) of the wavelength sweep is extracted as digital data of 2,048 points by setting an iterative frequency of the wavelength sweep to, for example, 40 kHz. However, the sampling frequency is not particularly limited thereto.

In accordance with an exemplary embodiment, the line-based interference light data created by the A/D converter 207 are input to the signal processing unit 201 and are temporarily stored in the memory 202. In addition, the signal processing unit 201 performs a FFT-based frequency decomposition for the interference light data to create data of a depth direction (line data). The signal processing unit 201 constructs an optical tomographic image at each position of the blood vessel from this line data. In some cases, the optical tomographic image is output to the LCD monitor 113 at a predetermined frame rate.

The signal processing unit 201 is further connected to an optical path length adjustment drive unit 209 and a communication unit 208. The signal processing unit 201 performs a control for the position (optical path length control) of the one-axis stage 224 using the optical path length adjustment drive unit 209.

In accordance with an exemplary embodiment, the communication unit 208 can be embedded with several drive circuits and communicates with the pull-back unit 102 under the control of the signal processing unit 201. Specifically, the communication unit 208 communicates with the pull-back unit 102 to supply a drive signal for rotating the third single mode fiber using the optical rotary joint of the pull-back unit 102 to a radial scanning motor, receive signals from the encoder unit 242 for detecting a rotational position of the radial motor, and supply a drive signal for guiding the third single mode fiber 274 at a predetermined velocity to a linear drive unit 243.

Note that it is assumed that the aforementioned processing of the signal processing unit 201 is also implemented by executing a predetermined program using a computer.

In the aforementioned configuration, if the probe 101 is placed in a blood vessel (for example, the coronary artery) as a diagnosis target for a patient, a light-transmissive flush liquid is discharged to the blood vessel through a tip of the probe 101 via a guiding catheter in response to a user's manipulation, which can be carried out in order to remove an influence of blood. In addition, as a user enters a scanning start instruction, the signal processing unit 201 drives the wavelength swept light source 203 to drive the radial scanning motor 241 and the linear drive unit 243 (hereinafter, a process of irradiating and receiving light by driving the radial scanning motor 241 and the linear drive unit 243 will be referred to as "scanning"). As a result, the wavelength-swept light from the wavelength swept light source 203 is supplied to the imaging core 250 through the aforementioned route. In this case, the imaging core 250 placed in the distal end position of the probe 101 moves along the rotation axis while it is rotated. Therefore, the imaging core 250 is rotated and moves along the blood vessel axis to emit light to an intravascular lumen and receive reflection light therefrom.

Figure 4:
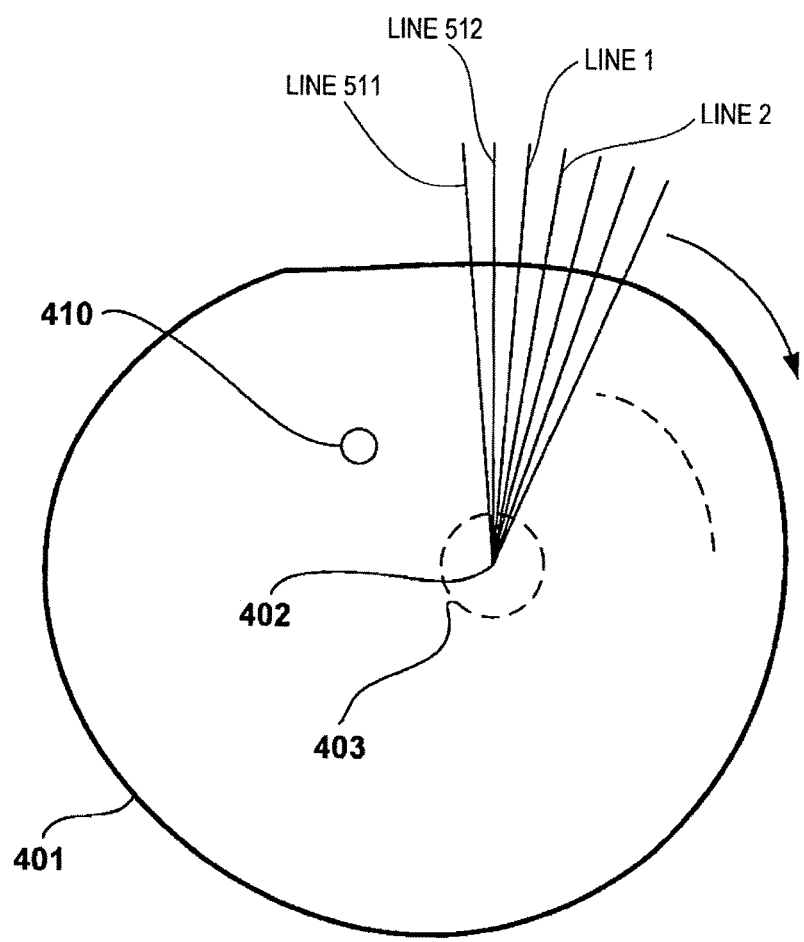
FIG. 4 is a diagram illustrating a process of creating a cross-sectional image.

Here, in accordance with an exemplary embodiment, a process for creating a single optical tomographic image will be described with reference to FIG. 4. FIG. 4 is a diagram for describing a process of reconstructing a cross-sectional image of a vascular lumen surface 401 where the imaging core 250 is placed. While the imaging core 250 is rotated by one revolution ($2\pi=360°$), the process of transmitting and receiving measurement light is performed several times. By performing the process of transmitting and receiving light once, a single line of data in a direction where the light is irradiated can be obtained. This data is subjected to the FFT so as to obtain line data representing a light reflection intensity (or absorbance amount) at each position directed in the radial direction from the rotation center position. Therefore, it is possible to obtain five hundred twelve (512) line data radially extending from the rotation center 402 by transmitting and receiving light, for example, five hundred twelve times for a single cycle. These five hundred twelve line data are dense in the vicinity of the rotation center and becomes sparse as it recedes from the rotation center position. In this regard, an interpolation process well known in the art is performed for the pixels in the empty space between each line to create a two-dimensional cross-sectional image that can be recognized by a human being. In addition, a three-dimensional vascular image can be obtained by connecting the created two-dimensional cross-sectional images to each other along the axis of the blood vessel. Note that, although the center position of the two-dimensional cross-sectional image matches the rotation center position of the imaging core 250, it is not the center position of the cross section of the blood vessel. In addition, light is reflected on a lens surface of the imaging core 250 and a surface of the catheter although it is weak. Therefore, several concentric circles are generated with respect to the rotation center axis as illustrated in reference numeral 403 of the drawings. Furthermore, reference numeral 410 in the drawings refers to an image representing that a guide wire is placed in that position. Note that, since the guide wire has an extremely high reflection light intensity, compared to blood vessel organs during construction of an optical tomographic image, the line data of the guide wire can be easily recognized.

Next, a configuration for forming an image using ultrasound waves and details of the processing therefor will be described.

Ultrasound scanning is performed simultaneously with the optical interference-based scanning described above. While the scanning is performed, and the probe 101 moves inside a catheter sheath by rotating the imaging core 250, ultrasound waves are emitted from the ultrasound transceiver housed in the imaging core 250, and their reflection waves are detected. For this reason, it is necessary to create a drive electric signal for driving the ultrasound transceiver housed in the imaging core 250 and receive a detection signal of the ultrasound wave output from the ultrasound transceiver. This operation of transmitting the drive signal and receiving the detected signal is performed by the ultrasound transmit/receive control unit 232. The ultrasound transmit/receive control unit 232 and the imaging core 250 are connected to each other through signal line cables 281, 282, and 283. Since the imaging core 250 is rotated, the signal line cables 282 and 283 are connected using a slip ring 231 provided in the pull-back unit 102. Note that, although the signal line cables 281 and 283 are connected using a single line in the drawings, a plurality of signal lines are housed in practice.

The ultrasound transmit/receive control unit 232 is operated under control of the signal processing unit 201 to drive the ultrasound transceiver housed in the imaging core 250 and generate pulsed ultrasound waves. The ultrasound transceiver converts the reflection wave from a blood vessel organ into an electric signal and supplies it to the ultrasound transmit/receive control unit 232. The ultrasound transmit/receive control unit 232 outputs the received ultrasound signal to the amplifier 233 for amplification. Then, the amplified ultrasound signal is supplied to the signal processing unit 201 as ultrasound data through the wave detector 234 and the A/D converter 235, and the ultrasound data are temporarily stored in the memory 202. Note that the A/D converter 235 samples the ultrasound signal output from the wave detector 234 at a frequency, for example, of 306 MHz as many as 2,000 points and creates a single line of digital data (ultrasound data). Note that, although the frequency is set to 306 MHz in this case, this is resulted by assuming that 2,000 points are sampled at a depth of 5 mm by setting a sound velocity to 1,530 m/sec. Therefore, the sampling frequency is not particularly limited thereto.

The signal processing unit 201 creates grayscale line data from the ultrasound data stored in the memory 202. Subsequently, similar to the reconstruction process of the optical cross-sectional image, each line data are two-dimensionally and radially arranged, and interpolation is applied, so that the ultrasound tomographic images for each intravascular position are created.

Next, a structure of the imaging core 250 of the probe portion 101 will be described with reference to FIG. 3.

Figure 3:
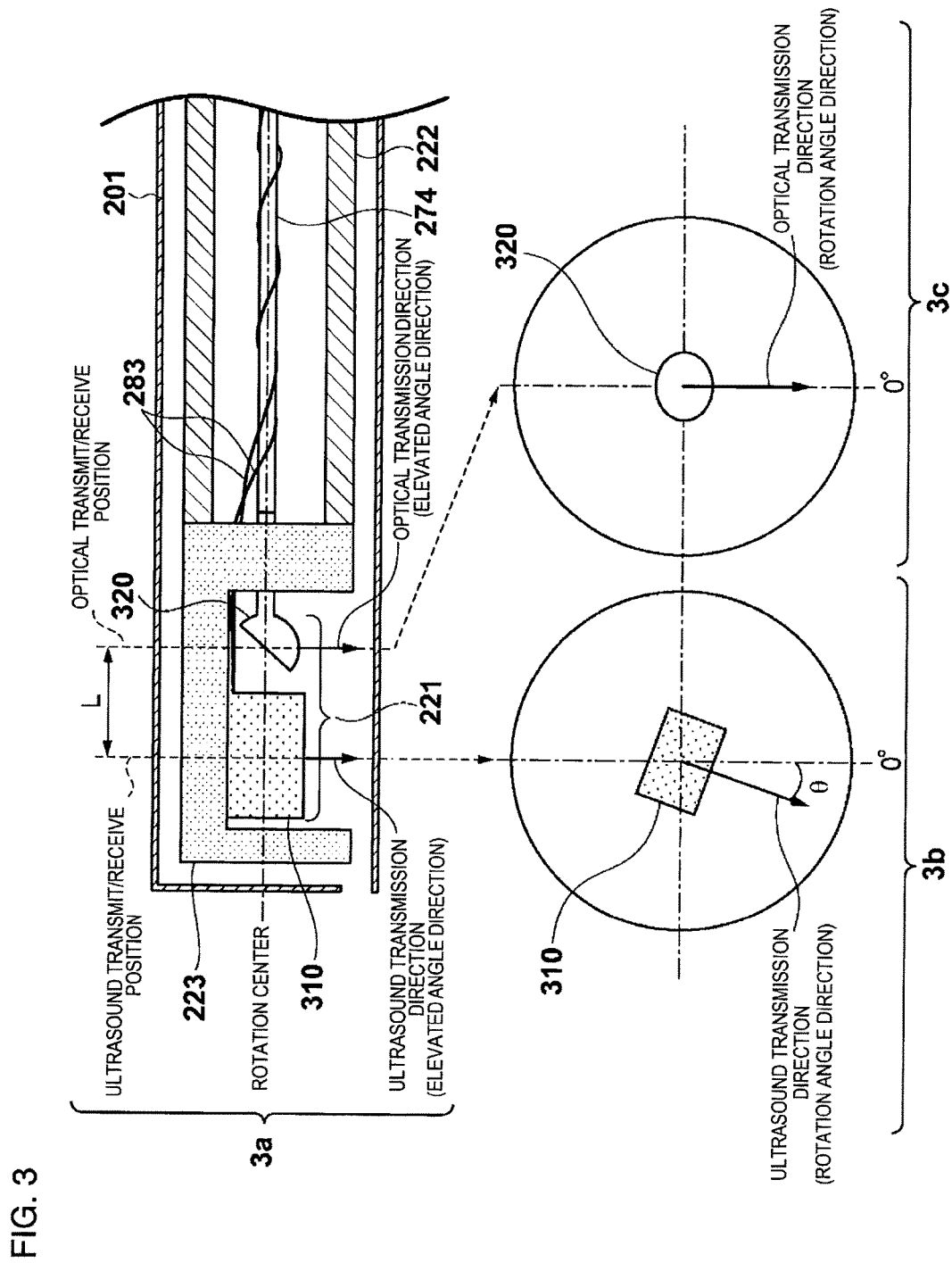
FIG. 3 is a diagram illustrating a cross-sectional configuration of an imaging core and arrangement of an ultrasound transceiver and an optical transceiver.

A diagram "3a" of FIG. 3 denotes a cross-sectional view illustrating the distal end portion of the probe portion 101. The distal end portion of the probe portion 101 includes a light-transmissive catheter sheath 201. As illustrated in FIG. 3, the transceiver 221 arranged inside the housing 223 includes an ultrasound transceiver 310 and an optical transceiver 320. Each of the ultrasound transceiver 310 and the optical transceiver 320 is arranged at a distance L along an axial direction on the rotation center axis (on the one-dotted chain line 3 of FIG. 3) of the drive shaft 222. The optical transceiver 320 includes a semispherical ball lens provided in the end portion of the third single mode fiber 274 as illustrated in FIG. 3. In this structure, the light incident from the third single mode fiber 274 is reflected on its sloped surface in the arrow direction of FIG. 3 and is transmitted to the blood vessel organ. In addition, the reflection light from the blood vessel organ is transmitted to the third single mode fiber 274.

The ultrasound transceiver 310 is placed in the distal end side of the probe portion 101, and the optical transceiver 320 is placed in the proximal end side of the probe portion 101. Note that the arrangement of the ultrasound transceiver 310 and the optical transceiver 320 is an exemplary embodiment of the disclosure, and the disclosure is not limited thereto. The optical transceiver 320 may be placed in the distal end side of the probe portion 101, and the ultrasound transceiver 310 may be placed in the proximal end side of the probe portion 101. Alternatively, they may be placed in the same position. In addition, the angle between the ultrasound wave transmission direction or the light transmission direction and the rotation direction may be set to an arbitrary angle, for example, such as 90° or 180°.

The ultrasound transceiver 310 and the optical transceiver 320 are installed in the housing 223 such that the ultrasound wave transmission direction (elevated angle direction) of the ultrasound transceiver 310 and the light transmission direction (elevated angle direction) of the optical transceiver 320 with respect to the axial direction of the drive shaft 222 are set, for example, to approximately 90°. Note that each transmission direction may be slightly deviated from 90° so that the reflection on an internal surface of the lumen of the catheter sheath 201 is not received by the probe portion 101.

An electric signal cable 283 connected to the ultrasound transceiver 310 and the third single mode fiber 274 connected to the optical transceiver 320 are housed in the drive shaft 222. The electric signal cable 283 is wound around the third single mode fiber 274 in a spiral shape.

Diagrams "3b" and "3c" of FIG. 3 show that the ultrasound transceiver 310 and the optical transceiver 320 are deviated by an angle θ in the signal emitting direction as seen from the rotation axis direction of the imaging core 250.

Here, in accordance with an exemplary embodiment, a rotation velocity of the imaging core during scanning can be set, for example, to "ω=9,600 rpm=160 revolutions/second" and a movement velocity of the same imaging core can be set, for example, to 10 mm/second. In addition, a distance between the ultrasound transceiver 310 and the optical transceiver 320 in the rotation axis direction is denoted by "L+ΔL." Here, the error range ΔL reflects a variation in the manufacturing process, and for example, the error range ΔL can be set, for example, to "ΔL=0" and "L=2 mm" for simplicity purposes. A case where the error range ΔL is not zero will be described separately. In addition, it is assumed that deviation angles θ of the emissions of the ultrasound transceiver 310 and the optical transceiver 320 of "3b" and "3c" of FIG. 3 are not known.

Figure 5:
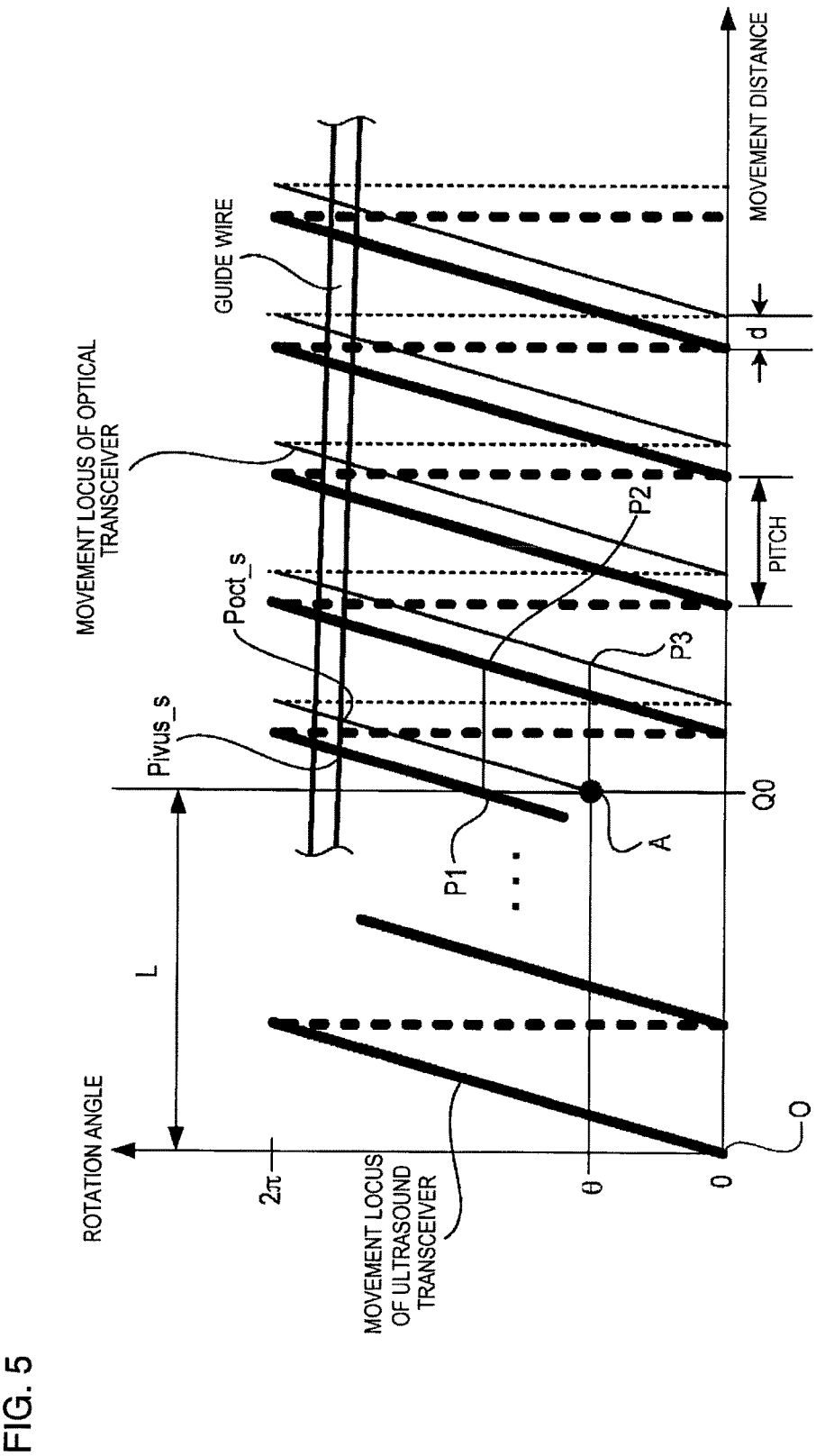
FIG. 5 is a diagram illustrating a relationship between movements of the optical transceiver and the ultrasound transceiver and a rotation angle according to an exemplary embodiment.

FIG. 5 illustrates a relationship between a movement distance along the axis of the blood vessel and a movement locus of the emission angle of the ultrasound transceiver 310 and the optical transceiver 320. In the following description, FIG. 5 will be described.

In FIG. 5, the horizontal axis (x-axis) refers to a movement distance, and the vertical axis (y-axis) refers to a rotation angle. Due to a rotation angle, if it reaches 2π (360°), the angle returns to zero. The origin indicates a position of the ultrasound transceiver 310 at the start of the scanning, and the emission direction of the ultrasound transceiver 310 at that time is regarded as an angle of zero. In addition, the position and the emission angle of the optical transceiver 320 at the scanning start timing are indicated by a point A in FIG. 5. In accordance with an exemplary embodiment, a movement distance (the "pitch" in FIG. 5) for a single revolution of the imaging core 250 is "10/160=0.0625 mm." Therefore, in order to move the ultrasound transceiver 310 to an intravascular x-coordinate position Q0 for the point A where the optical transceiver 320 is placed at the start of scanning, thirty two revolutions (32=2/0.0625) are necessary. In accordance with an exemplary embodiment, after the imaging core 250 is rotated thirty two times from the start of the scanning (movement by a distance L), data exist for each of the ultrasound transceiver 310 and the optical transceiver 320 in the same intravascular position. Therefore, both the ultrasound tomographic image and the optical tomographic image can be created in the same intravascular position.

The cross-sectional images are created on the basis of the line data (in this embodiment, five hundred twelve (512) line data) obtained by rotating the imaging core by one revolution.

In this regard, if a position of the ultrasound transceiver 310 on the locus in the position Q0 is defined as a point P1, and a position rotated from that point P1 by one revolution (2π) is defined as a point P2, an ultrasound tomographic image between the points P1 and P2 can be created using the five hundred twelve ultrasound line data therebetween. In addition, if a position rotated by one revolution from the point A is defined as a point P3, an optical tomographic image of nearly the same position as that of the ultrasound tomographic image can be created using the five hundred twelve optical interference-based line data between the points A and P3.

However, the points P1 and A which are the initial line data to create the cross-sectional image have different angles. Meanwhile, note that the angle θ where the point A is placed is originally unknown (for example, the error range ΔL is also unknown). Therefore, the ultrasound tomographic image using the point P1 as a starting point can be created from the ultrasound line data between the points P1 and P2, and the optical tomographic image using the point A as a starting point can be created from the optical interference line data between the points A and P3. However, since there is an angle difference between the points P1 and A serving as starting points for forming the image, the orientations of the two images do not match in most cases although they may match coincidentally. It is obvious that doctors desire to diagnose the two images by arranging the two images in the same direction. Therefore, there is a demand for improving such a mismatch of the direction.

In order to address such a problem, in accordance with an exemplary embodiment, it is necessary to temporarily prepare the ultrasound tomographic image and the optical tomographic image and then rotate at least one of the images to determine an angle at which the error range between the images is smallest. However, considering a case where, for example, only the optical tomographic image is rotated, the processing is performed by deviating the movement locus of the optical transceiver of FIG. 5 to the left side until it overlaps with the movement locus of the ultrasound transceiver, cutting out the locus from the angle θ of the point A and the angle of the point P1, and connecting the locus after the point P3. That is, the optical interference image corresponding to the ultrasound image at the point P2 does not have the same angle as that of the point P2 on the movement locus of the optical transceiver closest to the point P2, but becomes a point having the same angle as that of the point P2 on the movement locus of the optical transceiver before a single revolution.

In this regard, according to the disclosure, the ultrasound tomographic image and the optical tomographic image of the same orientation are created at the closest axial position. Therefore, instead of aligning the angles of the ultrasound tomographic image and the optical tomographic image after they are created temporarily, the angular alignment is performed for the line data before the tomographic image is created by applying interpolation.

In a case where the angular alignment is performed after the tomographic image is created temporarily, positions having nearly the same movement distance in FIG. 5 are selected as the line data for each of the ultrasound wave and the light. However, according to the disclosure, the line data are sequentially selected from a position having the closest movement distance at nearly the same angle. That is, since a movement distance from the point on the movement locus of the optical transceiver placed in the right side of the point P1 to the point on the movement locus of the optical transceiver placed in the right side of the point P2 is selected as one frame, data delayed by one revolution are not used partially unlike a case where the angle is aligned after the tomographic image is created temporarily. Therefore, two closer tomographic images can be created.

As a method of identifying a line or a group of lines having the same feature out of the line data of each of the ultrasound tomographic image and the optical interference tomographic image, a method of recognizing a blood vessel shape may be employed. For example, it is possible to identify a line or a group of lines having the same feature out of each line data of the ultrasound tomographic image and the optical interference tomographic image on the basis of the features of the vascular lumen such as a shape, a bifurcation, and a lesion area.

As another method, a line or a group of lines having the same feature out of each line of the ultrasound tomographic image and the optical interference tomographic image may be identified using an object artificially inserted into the blood vessel. For example, a feature of a secured object such as a stent, a guide wire, and a marker provided in the catheter sheath may be used to identify a line or a group of lines having the same feature out of each line of the ultrasound tomographic image and the optical interference tomographic image.

In this regard, considering a fact that the scanning is performed while the guide wire is placed inside a blood vessel, the processing is performed by using the guide wire as a reference. A relating principle will be described below. Note that it is known that, since the guide wire is formed of metal, a reflection intensity against an emitted signal is significantly stronger than that of a blood vessel organ, in both cases of the ultrasound wave and the optical interference. Therefore, the line data obtained from a place where the guide wire exists can be relatively easily identified.

Figure 6:
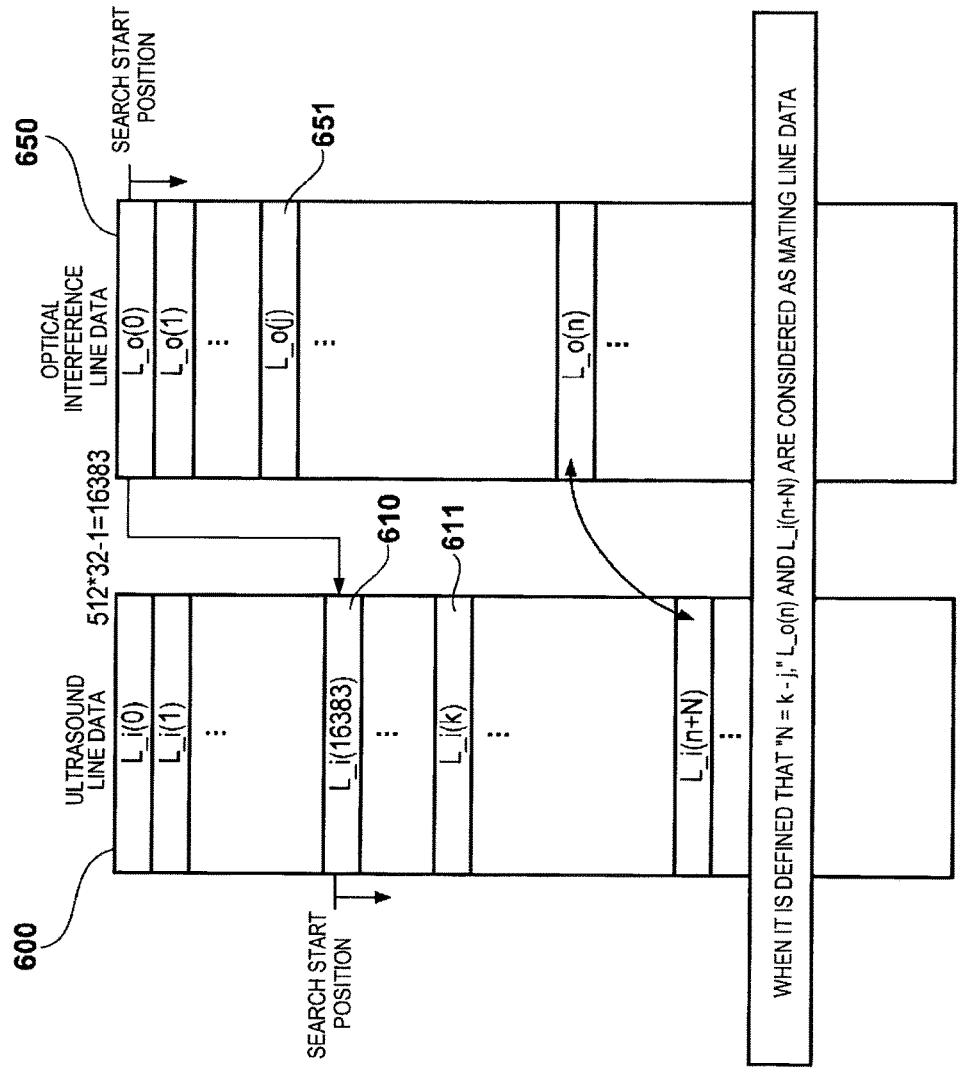
FIG. 6 is a diagram illustrating a memory storage state of the ultrasound line data and the optical interference line data.

FIG. 6 illustrates the ultrasound line data 600 and the optical interference line data 650 can be accumulated and stored in the memory 202 through the scanning. The storing sequence of the line data is illustrated in a top-down manner in FIG. 6. By setting the initial line as the zeroth line, the (n)-th ultrasound line data is denoted by "L_i(n)," and the (n)-th optical interference line data is denoted by "L_o(n)."

The ultrasound line data on the origin of FIG. 5 corresponds to "L_i(0)," and the optical interference line data on the point A corresponds to "L_o(0)."

The line data corresponding to the point P1 of the ultrasound line data of FIG. 5 is the (16384)-th line data (=32×512) from the head. Therefore, the line data 610 corresponding to the point P1 becomes "L_i(16383)."

In this embodiment, the search is performed downward in FIG. 6 (rotation direction) starting from the ultrasound line data L_i(16383) to find the line data 611 indicating existence of the guide wire. This line data is denoted by "L_i(k)." This line data 611 corresponds to the point Pivus_s in FIG. 5.

In addition, the search is performed downward in FIG. 6 (rotation direction) starting from the optical interference line data L_o(0) to find the line data 651 indicating existence of the guide wire. This line data is denoted by "L_o(j)." This line data 651 corresponds to the point Poct_s in FIG. 5.

According to the disclosure, the line data 611 and the line data 651 are regarded as the mating line data.

In accordance with an exemplary embodiment, by regarding the line data 611 as line data of a predetermined angle direction (for example, a zero-hour direction), an ultrasound tomographic image is reconstructed using five hundred twelve line data therefrom. In addition, by regarding the line data 651 as line data arranged in the same direction as that of the line data 611, a reconstructed optical tomographic image is created using five hundred twelve line data starting from the line data 651. The created ultrasound tomographic image and the created optical tomographic image are aligned in nearly the same position with respect to the axis of the blood vessel and in the same orientation.

As recognized from FIG. 5, since each movement locus is created such that the deviation d is smaller than, for example, 0.03125 mm which is a half of one pitch, an angle difference between the points Pivus_s and point Poct_s is substantially zero. Therefore, a pair of the ultrasound tomographic image and the optical tomographic image can be aligned in the same direction.

As apparent from the aforementioned description, the index "k" of the ultrasound line data 611 (L_i(k)) and the index "j" of the optical interference line data 651 (L_o(j)) are determined once, and a difference between the indices k and j is set as an offset number N (N=k−j). In addition, the ultrasound line data corresponding to arbitrary optical interference line data L_o(n) becomes "L_ivus(n+N)."

In the aforementioned example, the error range ΔL is not included in the distance L in the rotation axis direction between the ultrasound transceiver 310 and the optical transceiver 320. However, since each movement locus is formed to have a deviation d smaller than a half of one pitch, the same processing is resulted even when there is an error range ΔL.

Figure 7:
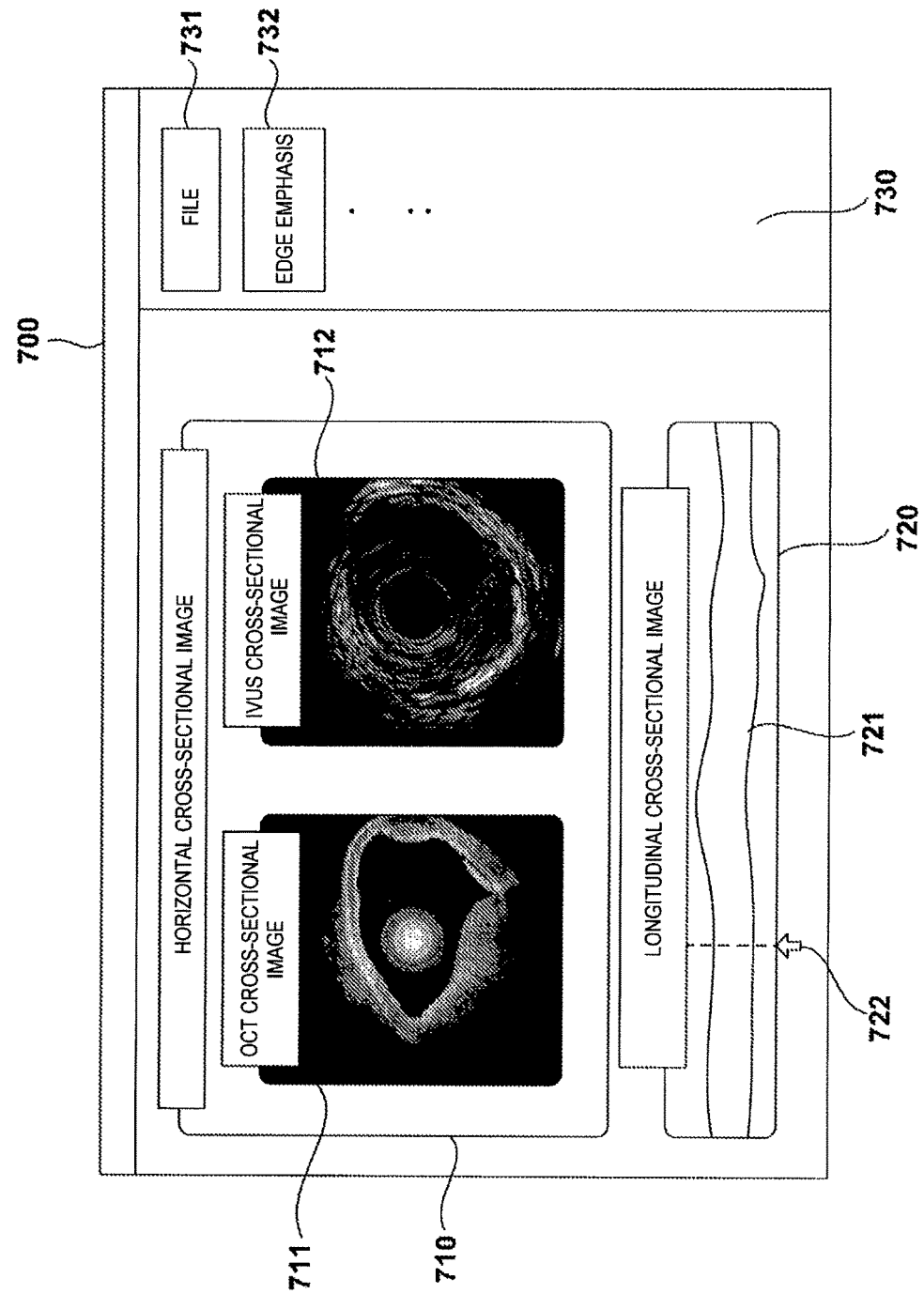
FIG. 7 is a diagram illustrating an exemplary display screen according to an exemplary embodiment.

FIG. 7 illustrates a window 700 displayed on an LCD display 113 after the scanning is completed. This window 700 is roughly divided into display areas 710, 720, and 730.

The display area 710 includes a display area 711 for displaying an optical tomographic image (illustrated as the "OCT cross-sectional image" in FIG. 7) on a plane orthogonal to the axis of the blood vessel, and a display area 712 for displaying an ultrasound tomographic image (illustrated as the "IVUS cross-sectional image" in FIG. 7) on a plane orthogonal to the axis of the blood vessel.

In accordance with an exemplary embodiment, an area for displaying an image obtained by overlapping both the images may also be provided, and a single image may also be displayed solely.

The display area 720 shows a longitudinal cross-sectional image 721 along the axis of the blood vessel when the scanning is performed. In this longitudinal cross-sectional image 721, an image of a single line in the vertical direction can be formed by creating a plurality of frames by connecting, for example, the (n)-th line data L_o(n+512*s) of the (s)-th frame of, for example, the optical interference line data 650 accumulated in the memory 202 and the line data L_o(n+512*s+256) perfectly opposite to the (n)-th line data L_o(n+512*s).

The longitudinal cross-sectional image 721 may be created from the ultrasound line data. In addition, the longitudinal cross-sectional image 721 may be created from both the ultrasound line data and the optical interference line data by considering the offset number N.

A position of the marker 722 can be moved by a user (for example, a doctor) in the horizontal direction by controlling the mouse 114. On the display area 710 described above, an ultrasound tomographic image and an optical interference tomographic image corresponding to the position indicated by the marker 722 are displayed.

Buttons for instructing various processes are arranged on the display area 730. For example, a file button 731 for storing the line data obtained through scanning or reading of the data stored in the past, a button 732 for selecting an edge emphasis level of the image processing, and the like can be arranged on the display area.

Since various buttons displayed on the display area 730 do not relate to the gist of the disclosure, they will not be described herein. In the following description, a processing of the signal processing unit 201 when the movement of the marker 722 is instructed will be described.

Since the marker 722 can be moved in the horizontal direction, its horizontal position is denoted by "Mx."

The signal processing unit 201 obtains the corresponding optical interference line data L_o(m) from the position Mx after moving the marker 722. Here, "m" is an integer multiple of "512," and is obtained by subtracting "1" from the frame number corresponding to the position Mx. In addition, the signal processing unit 201 creates the optical interference tomographic image using five hundred twelve optical interference line data L_o(m) to L_o(m+511) while the line data L_o(m) is aligned in a predetermined direction (in this embodiment, a zero-hour direction). In addition, at this time point, the offset number N (refer to FIG. 6) between the optical interference line data and the ultrasound line data is determined through the processing described above. Therefore, the signal processing unit 201 creates the ultrasound tomographic image using ultrasound line data L_i(m+N) to L_i(m+N+511) while the line data L_i(m+N) is aligned in a predetermined direction (in this embodiment, a zero-hour direction). In addition, the signal processing unit 201 displays the created ultrasound tomographic image and the created optical tomographic image on the display area 710. As a result, even when a user moves the marker 722 to any position, the ultrasound tomographic image and the optical tomographic image can be displayed in substantially the same position as that of the marker 722 and in the same orientation as the images aligned in a predetermined direction.

Figure 8:
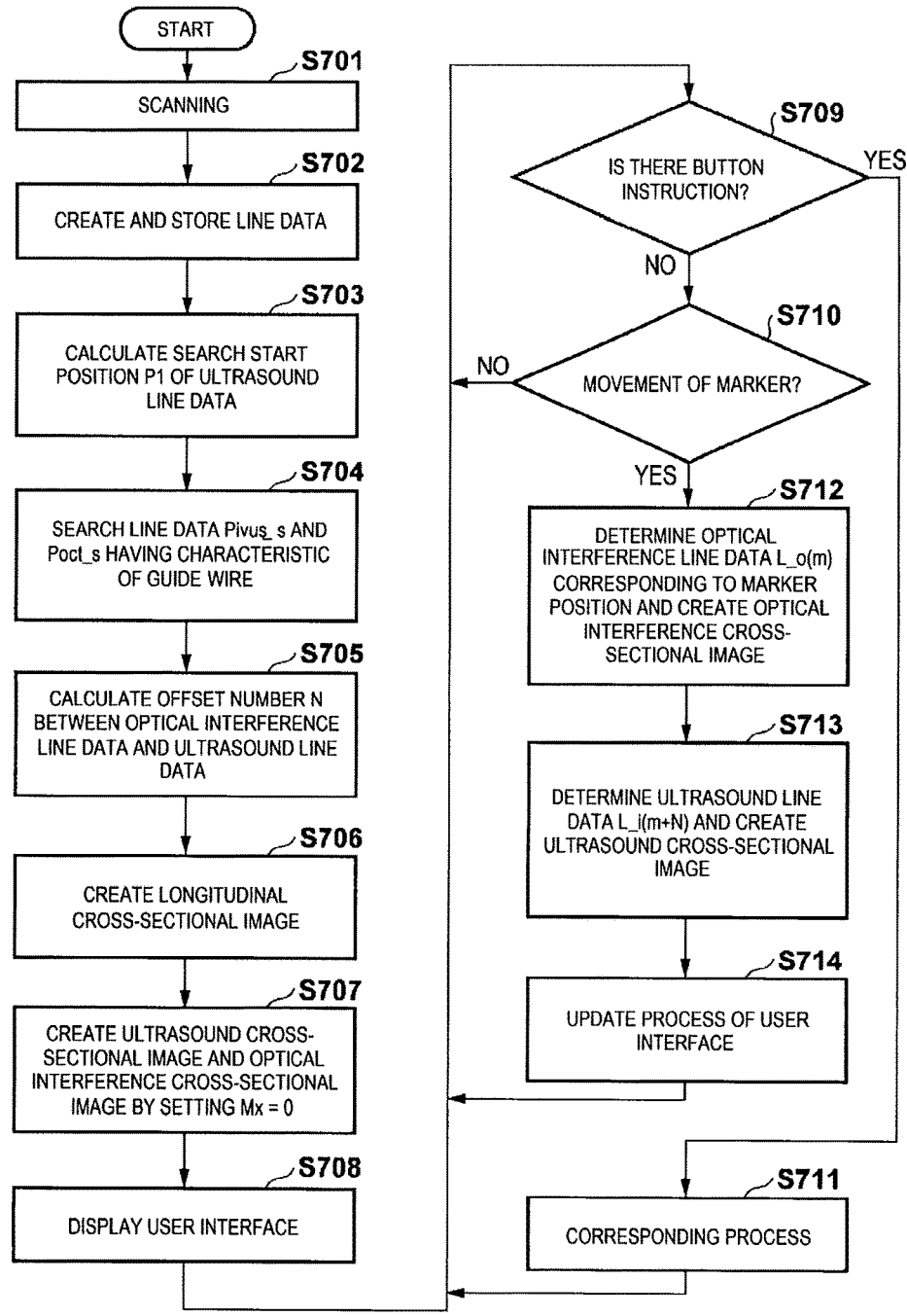
FIG. 8 is a flowchart illustrating a processing sequence of a signal processing unit according to an exemplary embodiment.

In accordance with an exemplary embodiment, a processing sequence of the signal processing unit 201 according to an embodiment will be described with reference to FIG. 8. The program relating to FIG. 8 stored in the hard disk 210 is loaded in the memory 202 and is executed by the signal processing unit 201.

The tip of the probe 101 is inserted into a position of a target blood vessel of a patient. If a scanning instruction is input from a user, the signal processing unit 201 performs scanning by controlling the pull-back unit 102 (step S701). As a result, the optical interference data and the ultrasound interference data are obtained from the A/D converters 207 and 235. The signal processing unit 201 appropriately processes these data to convert them to line data and accumulates them in the memory 202 (step S702). As a series of scanning procedures are completed, the signal processing unit 201 calculates which line includes the point P1 at which the ultrasound transceiver 310 reaches the same position as that of the optical transceiver at the start of the scanning, that is, a first offset number N1 based on an arrangement relationship on the design between the ultrasound transceiver and the optical transceiver, from the distance L between the ultrasound transceiver 310 and the optical transceiver 320 of the imaging core 250 and the movement velocity of the imaging core 250 employed in the scanning (step S703).

The first offset number N1 can be calculated on the basis of a formula "{L/(v/w)}×K," where "L" denotes a distance between the ultrasound transceiver 310 and the optical transceiver 320, "w" denotes a rotation velocity [round/second] of the imaging core 250, "v" denotes a movement velocity [mm/second] of the imaging core 250, and "K" denotes the number of lines [line/round] obtained per one revolution of the imaging core 250.

The signal processing unit 210 performs scanning in the rotation direction starting from the head line data in the case of the optical interference line data or starting from the line data of the point P1 indicated by the offset number from the head in the case of the ultrasound line data and searches the line data where the existence of the guide wire is recognized, that is, the points Poct_s and Pivus_s of FIG. 5. In addition, the signal processing unit 201 calculates a difference of the movement distance or direction between the points Poct_s and Pivus_s in and detects the points Poct_s and Pivus_s at which the difference is equal to or smaller than a half of the pitch, so that the difference is set as the deviation d. Furthermore, if the number of lines included in the deviation d is calculated as a second offset number N2, an offset number N is obtained by adding the second offset number to the first offset number (step S705). Note, for example, that the second offset number N2 is generated due to a manufacturing deviation and a fluctuation of the rotation number.

Then, the signal processing unit 201 creates a longitudinal vascular cross-sectional image using the optical interference line data (step S706). Note that this longitudinal vascular cross-sectional image may be created using the ultrasound line data or may be created from both the ultrasound line data and the optical interference line data by considering the offset number N. In addition, it may be possible to allow a user to select which one will be employed.

In addition, the ultrasound tomographic image and the optical interference tomographic image are created by setting the initial position of the marker 722 as "Mx=0" (step S707). Specifically, the optical tomographic image is created from the optical interference line data L_o(m) to L_o(m+511) corresponding to "Mx=0." Here, although "m" is an integer multiple of "512," it is set to zero (m=0) because "Mx=0." In addition, the signal processing unit 201 creates the ultrasound tomographic image from the ultrasound line data L_i(m+N) to L_i(m+N+511) using the offset number N which is a coefficient of the position correction process. In any cross-sectional image, the head line is created by assuming that it is aligned in a predetermined angle (in this embodiment, a zero-hour direction).

The signal processing unit 201 displays a graphical user interface illustrated in FIG. 7 on the LCD display 113 and waits for an event selected by a user.

For example, in a case where a movement instruction for the marker 722 is issued, an optical interference line data L_o(m) (where "m" denotes an integer multiple of "512") of the frame corresponding to the position Mx of the moved marker 722 is obtained, and an optical tomographic image is created from the optical interference line data L_o(m) to L_o(m+511). In addition, the signal processing unit 201 creates the ultrasound tomographic image from the ultrasound line data L_o(m+N) to L_o(m+N+511). In addition, the signal processing unit 201 updates the display using the created optical tomographic image and the created ultrasound tomographic image.

As described above, according to this embodiment, the ultrasound tomographic image and the optical tomographic image can be displayed in substantially the same position with respect to the axis of the blood vessel and in the same orientation. In addition, since the offset line number N for mating the line data regarded as being located in the same orientation and in the same position with respect to the axis of the blood vessel is determined in the state of the line data of the ultrasound wave and the optical interference, it is not necessary to perform a process of rotating the cross-sectional image for aligning them in the same orientation. Therefore, it is possible to reduce a load of the signal processing unit 201 and update the screen fast in response to a movement instruction of the marker 722.

Note that, although the optical transceiver 320 of the imaging core 250 is located closer to the probe portion 102 relative to the ultrasound transceiver 310 in this embodiment, this relationship may be reversed. In the reversed case, it is conceived that the relationship of each line data stored in the memory 202 is also reversed.

Although the processes performed until the display on the GUI and the screen update process in response to a user's instruction are shown as a single processing program in the flowchart of FIG. 7, the disclosure is not limited thereto. That is, since recent operating systems are even-driven types, the processes performed until the display on the GUI and the update process in response to a user's instruction may be independent procedures that start execution depending on each event.

Some numerical values referred to in the embodiments are just exemplary for easy understanding purposes, and they are not intended to limit the disclosure. Although five hundred twelve (512) line data are obtained through a single revolution in the embodiments, for example, two thousand forty eight (2,048) ultrasound line data may also be obtained.

Although the feature of the line is identified by extracting the feature from each line data in the embodiments, the disclosure is not limited thereto. Instead, the feature of the line may be identified by, once the ultrasound tomographic image and the optical tomographic image are created, extracting the feature from the tomographic images and determining which position of the line data relates to the feature.

Although the position correction process using the offset number N is performed immediately before creation of the tomographic image in the embodiments, the disclosure is not limited thereto. Instead, correction may be performed as an initial position correction process by reassigning indices of each line data using the first offset number N1, that is, shifting the data storage area, and the same position correction process as that of the embodiment may be performed using the second offset number N2.

According to the disclosure, correction of the radial scale may also be performed. For example, the correction may be performed by using a sound velocity in the case of the ultrasound line data and using a difference of the refractive index in the case of the optical line data. In addition, the correction may be included in any processing step depending on purposes. For example, in a case where the feature of the radial direction that changes in the scanning direction is identified, the correction is preferably performed before the feature is identified. In particular, in a case where the feature of the radial direction is not identified, the correction may be included in any processing step. For example, the correction may be performed immediately before the tomographic image is created.

In a case where correction of the radial direction is performed after the feature is identified, mating between the ultrasound line data and the optical interference line data is already completed. Therefore, alignment can be performed such that they have relatively the same radial scale. Although it is important to match a scale of the actual measurement target, it is also important to relatively align the scales of the two types of tomographic images.

Although the catheter sheath or the flush liquid is light-transmissive in the embodiments, they are preferably formed of a material which allows an ultrasound wave to easily transmit and has physical properties such as acoustic impedance and a refractive index not significantly different from those of neighboring materials.

As recognized from the aforementioned embodiment, most of the processes of the embodiment are performed using the signal processing unit 201 configured as a microprocessor. Therefore, since functions of the microprocessor are implemented by executing the program, naturally, such a program is included in the scope of the disclosure. In addition, a typical program is stored in a computer readable storage medium such as a CD-ROM or a DVD-ROM and is executable by setting it on a reader device such as a CD-ROM drive provided in a computer and copying or installing it in a system. Therefore, it is also obvious that the relating computer readable storage medium is also included in the scope of the disclosure.

The disclosure is not limited to those the aforementioned embodiments, but various changes and modifications may be possible without departing from the spirit and scope of the disclosure. Therefore, the following claims are appended to announce the scope of the disclosure.

The detailed description above describes an imaging apparatus for diagnosis, a control method therefore, a program, and a computer readable storage medium. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A control method of an imaging apparatus for diagnosis, the imaging apparatus for diagnosis being configured to create an ultrasound tomographic image and an optical tomographic image inside an examination target object to which an imaging core moves using a probe that houses the imaging core provided with an ultrasound transceiver and an optical transceiver by performing scanning moves the imaging core along an axial direction of the probe while rotating the imaging core, the control method comprising:

obtaining ultrasound line data oriented in a radial direction from a rotation center on a basis of a signal obtained by executing the scanning;

obtaining optical interference line data oriented in a radial direction from the rotation center on a basis of a signal obtained by executing the scanning;

identifying a line or a group of lines having a same feature out of each line data of the ultrasound tomographic image and the optical tomographic image;

determining segmentation positions for a bundle of lines corresponding to at least a single frame included in each tomographic image from each line data of the ultrasound tomographic image and the optical tomographic image with respect to the identified line or group of lines; and creating a tomographic image from the determined bundle of lines.

2. The control method according to claim 1, comprising: artificially inserting the same feature into a blood vessel.

3. The control method according to claim 2, wherein the same feature, which is artificially inserted into the blood vessel, is a stent, a guide wire, or a marker in a catheter sheath.

4. The control method according to claim 1, wherein the same feature is a shape of a blood vessel.

5. The control method according to claim 1, wherein the process of identifying has a process of creating a tomographic image from each line data of the ultrasound tomographic image and the optical tomographic image, and performing the identification using the tomographic image obtained from the process of creating the tomographic image.

6. A program read and executed by a computer to allow the computer to execute each step of the control method of the imaging apparatus for diagnosis according to claim 1.

7. A program read and executed by a computer to allow the computer to execute each step of the control method of the imaging apparatus for diagnosis according to claim 2.

8. A program read and executed by a computer to allow the computer to execute each step of the control method of the imaging apparatus for diagnosis according to claim 4.

9. A program read and executed by a computer to allow the computer to executed each step of the control method of the imaging apparatus for diagnosis according to claim 5.

10. A non-transitory computer readable storage medium containing a computer program having computer readable code embodied to carry out a method of controlling an imaging apparatus for diagnosis, the imaging apparatus for diagnosis being configured to create an ultrasound tomographic image and an optical tomographic image inside an examination target object to which an imaging core moves using a probe that houses the imaging core provided with an ultrasound transceiver and an optical transceiver by performing scanning moves the imaging core along an axial direction of the probe while rotating the imaging core, the method of controlling the imaging apparatus for diagnosis comprising:

obtaining ultrasound line data oriented in a radial direction from a rotation center on a basis of a signal obtained by executing the scanning;

obtaining optical interference line data oriented in a radial direction from the rotation center on a basis of a signal obtained by executing the scanning;

identifying a line or a group of lines having a same feature out of each line data of the ultrasound tomographic image and the optical tomographic image;

determining segmentation positions for a bundle of lines corresponding to at least a single frame included in each tomographic image from each line data of the ultrasound tomographic image and the optical tomographic image with respect to the identified line or group of lines; and creating a tomographic image from the determined bundle of lines.

11. The non-transitory computer readable medium according to claim 10, comprising:

artificially inserting the same feature inserted into a blood vessel.

12. The non-transitory computer readable medium according to claim 11, wherein the same feature, which is artificially inserted into the blood vessel, is a stent, a guide wire, or a marker in a catheter sheath.

13. The non-transitory computer readable medium according to claim 10, wherein the same feature is a shape of a blood vessel.

14. The non-transitory computer readable medium according to claim 10, wherein the process of identifying has a process of creating a tomographic image from each line data of the ultrasound tomographic image and the optical tomographic image, and performing the identification using the tomographic image obtained from the process of creating the tomographic image.

15. An imaging apparatus for diagnosis configured to create an ultrasound tomographic image and an optical tomographic image inside an examination target object to which an imaging core moves using a probe that houses the imaging core provided with an ultrasound transceiver and an optical transceiver by performing scanning moves the imaging core along an axial direction of the probe while rotating the imaging core, the imaging apparatus comprising:

a processor configured to:

obtain ultrasound line data oriented in a radial direction from a rotation center on a basis of a signal obtained by executing the scanning;

obtain optical interference line data oriented in the radial direction from the rotation center on a basis of a signal obtained by executing the scanning;

identify a line or a group of lines having a same feature out of each line data of the ultrasound tomographic image and the optical tomographic image;

determine segmentation positions for a bundle of lines corresponding to at least a single frame included in each tomographic image from each line data of the ultrasound tomographic image and the optical tomographic image with respect to the identified line or group of lines; and create a tomographic image from the determined bundle of lines.

16. The imaging apparatus for diagnosis according to claim 15, wherein the same feature is artificially inserted into a blood vessel.

17. The imaging apparatus for diagnosis according to claim 16, wherein the same feature, which is artificially inserted into the blood vessel is a stent, a guide wire, or a marker in a catheter sheath.

18. The imaging apparatus for diagnosis according to claim 15, wherein the same feature is a shape of a blood vessel.

19. The imaging apparatus for diagnosis according to claim 15, wherein the processor is further configured to:

create a tomographic image from each line data of the ultrasound tomographic image and the optical tomographic image, and perform the identification using the created tomographic image obtained from a process of creating the tomographic image.

20. The imaging apparatus for diagnosis according to claim 15, further comprising:

a display unit configured to display the tomographic image created from the determined bundle of lines.

* * * * *